(12) United States Patent
Zhou et al.

(10) Patent No.: US 10,392,634 B2
(45) Date of Patent: Aug. 27, 2019

(54) METHOD FOR HIGH-EFFICIENCY PRODUCTION OF PINORESINOL USING AN $H_2O_2$ AUTO-SCAVENGING CASCADE

(71) Applicants: Jingwen Zhou, Wuxi (CN); Jian Chen, Wuxi (CN); Yongkun Lv, Wuxi (CN); Guocheng Du, Wuxi (CN)

(72) Inventors: Jingwen Zhou, Wuxi (CN); Jian Chen, Wuxi (CN); Yongkun Lv, Wuxi (CN); Guocheng Du, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 1 day.

(21) Appl. No.: 15/472,003

(22) Filed: Mar. 28, 2017

(65) Prior Publication Data

US 2018/0171367 A1 Jun. 21, 2018

(30) Foreign Application Priority Data

Dec. 15, 2016 (CN) .......................... 2016 1 1158402

(51) Int. Cl.
| | |
|---|---|
| *C12P 7/22* | (2006.01) |
| *C12N 9/04* | (2006.01) |
| *C12N 9/08* | (2006.01) |
| *C12N 1/20* | (2006.01) |
| *C12N 15/00* | (2006.01) |
| *C07H 21/04* | (2006.01) |
| *C12N 15/62* | (2006.01) |
| *C12P 17/18* | (2006.01) |

(52) U.S. Cl.
CPC ............... *C12P 7/22* (2013.01); *C12N 1/20* (2013.01); *C12N 9/0006* (2013.01); *C12N 9/0065* (2013.01); *C12N 15/62* (2013.01); *C12P 17/181* (2013.01); *C12Y 101/03038* (2013.01); *C12Y 111/01007* (2013.01)

(58) Field of Classification Search
None
See application file for complete search history.

(56) References Cited

PUBLICATIONS

Ricklefs. Two-Step One-Pot Synthesis of Pinoresinol from Eugenol in an Enzymatic Cascade. ChemCatChem 2015, 7, 1857-1864. Published online on Jun. 3, 2015.*
Lazzarotto. Revisiting the non-animal peroxidase superfamily. Trends Plant Sci 20(12):807-813. 2015.*

(Continued)

*Primary Examiner* — Yong D Pak
(74) *Attorney, Agent, or Firm* — Lili Chen

(57) ABSTRACT

The present invention provides a method for high-efficiency production of pinoresinol by use of an $H_2O_2$ auto-scavenging enzymatic cascade. It uses eugenol as the substrate, which is relatively inexpensive and is industrially available. It uses an enzymatic cascade to remove $H_2O_2$ produced in the process of pinoresinol synthesis, thereby reducing its inhibitory effect on the enzyme activity. In addition, the present invention uses whole cells as a catalyst, which can continuously regenerate cofactors needed by the enzyme, thus eliminating the need for exogenous addition of expensive cofactors during the reaction. The yield of the present invention can reach 7.12 g/L and the conversion rate is 61.55%.

5 Claims, 12 Drawing Sheets

Specification includes a Sequence Listing.

(56) References Cited

PUBLICATIONS

De Weert. Heterologous expression of peroxidases. In: Torres E, Ayala M, editors. Biocatalysis based on heme peroxidases: Peroxidases as potential industrial biocatalysts. Berlin, Heidelberg: Springer Berlin Heidelberg. p. 315-333. 2010.*
Lucas. A0A140N7A8—UniProtKB Database. May 2016.*
Biorad. Protein Expression and Purification Series. 2011.*
Carvalho. Enzymatic and whole cell catalysis: Finding new strategies for old processes. Biotechnology Advances 29 (2011) 75-83.*

* cited by examiner

METHOD FOR HIGH-EFFICIENCY PRODUCTION OF PINORESINOL USING AN H₂O₂ AUTO-SCAVENGING CASCADE

CROSS-REFERENCES AND RELATED APPLICATIONS

This application claims the benefit of priority to Chinese Application No. 201611158402.X, entitled "A method for high-efficiency production of pinoresinol using an H₂O₂ auto-scavenging cascade", filed Dec. 15, 2016, which is herein incorporated by reference in its entirety.

BACKGROUND OF THE INVENTION

Field of the Invention

The present invention relates to the field of biological and chemical engineering, and particularly relates to a method for high-efficiency production of pinoresinol using an $H_2O_2$ auto-scavenging cascade.

Description of the Related Art

Pinoresinol is one of the simplest natural lignans in the group of phytoestrogens. Pinoresinol serves as a precursor of mammalian lignans enterodiol and enterolactone, which are produced in the mammalian proximal colon and have great health-supporting effects. Pinoresinol has activities of anti-oxidation, anti-inflammation, and hepato-protection, and exerts inhibitory effects to tumor growth, skin-pigmentation, and HIV-1 replication. Pinoresinol is also a potential inhibitory agent for type 2 diabetes mellitus (T2DM), microvascular damage, and fungal infection.

Currently, pinoresinol is mainly isolated from the seeds, fruits, and vegetables of some grains with low efficiency and low yields. For example, only 29 mg pinoresinol can be isolated from 100 g fresh sesame seeds. On the other hand, the requirement of multiple steps and extensive work-up makes chemical synthesis of pinoresinol a difficult task.

Although enzymatic approaches for pinoresinol biosynthesis have been developed, the existing methods have low selectivity and the product concentration is low. Moreover, expensive coniferyl alcohol was used as the substrate in the reaction. Recently, a promising two-step enzymatic cascade was designed by E. Ricklefs et al, which used inexpensive eugenol as the substrate. By using this cascade, eugenol was converted into coniferyl alcohol by vanillyl alcohol oxidase (VAO), and coniferyl alcohol was subsequently converted into pinoresinol by laccase. Eugenol is a natural substrate that is widely available, cheap, and can be isolated from the essential oil of the clove tree *Syzygium aromaticum* on an industrial scale. Pinoresinol concentration reached 4.4 mM (1.6 g/L) under optimized condition. However, two problems exist in this design. Firstly, VAO uses molecular oxygen as an electron acceptor, and one molar $H_2O_2$ was produced during the production of one molar coniferyl alcohol (Equation 1). The accumulation of $H_2O_2$ is toxic to the host cell and inhibits the enzymes. Secondly, the activity of VAO is cofactor dependent. The enzymes are not stable in the in vitro environment compared to the intracellular counterpart. And the cofactor FAD was needed for the activity of VAO.

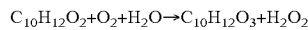

(1)

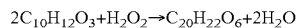

(2)

DETAILED DESCRIPTION

To solve the aforementioned problems, the present invention provides a two-step enzymatic method for converting eugenol to pinoresinol by use of a VAO and a peroxidase. The inexpensive industrially available eugenol is used as the substrate to produce coniferyl alcohol by use of VAO. Coniferyl alcohol was subsequently converted into pinoresinol by use of peroxidase, which uses $H_2O_2$ as an electron acceptor and reduces it to $H_2O$ (Equation 2). The advantages of this cascade are as follows: (1) Eugenol is used as the substrate, which is inexpensive and industrially available. (2) $H_2O_2$ is used as the electron acceptor and automatically scavenged, which eliminated its inhibition to the enzymes and detoxified the extra $H_2O_2$. (3) The two steps of the cascade are accomplished in one single cell, which eliminates the inefficient transmembrane transportation. (4) The intracellular environment continuously generates the needed cofactors for VAO, eliminating the requirement of external addition of expensive cofactors. (5) The intracellular environment provides a more stable condition for the enzymes than in vitro conditions.

The goal of the present invention is to provide a method for high-efficiency production of pinoresinol using an $H_2O_2$ auto-scavenging enzymatic cascade. The whole cell harboring the enzymes was used as the catalyst and eugenol was used as the substrate.

Eugenol is a main component of clove oil, which can be isolated from the clove tree *Syzygium aromaticum*. Clove oil can also be directly used as the substrate to eliminate the cost of purification.

The enzymatic cascade comprises a VAO and peroxidase. VAO is used to produce coniferyl alcohol from eugenol, and peroxidase is used to produce pinoresinol from coniferyl alcohol.

The described $H_2O_2$ auto-scavenging refers to the reactions that $H_2O_2$ produced by VAO is utilized by peroxidase as an electron acceptor and reduced to $H_2O$. This detoxified the extra intracellular $H_2O_2$.

The described VAO is from *Penicillium simplicissimum* (PsVAO). The amino acid sequence and DNA sequence of the VAO are SEQ ID NO:1 and SEQ ID NO: 2, respectively.

The described peroxidase is from *Escherichia coli* BL21 (DE3). The amino acid sequence and DNA sequence of the peroxidase were SEQ ID NO:3 and SEQ ID NO: 4, respectively.

The described whole cell refers to the recombinant *E. coli* BL21 (DE3) cell, which harbors PsVAO and peroxidase, or the fusion protein of PsVAO and peroxidase.

A ePathBrick vector pET-28a(PB) is used for the construction and expression of the cascade of VAO and peroxidase or a fusion protein of the two enzymes. The DNA sequence of the vector was SEQ ID NO: 5.

In a preferred embodiment, the reaction conditions are as follows, the amount of recombinant *E. coli* cell OD600=18±1, eugenol concentration 0.5% (v/v), temperature 25° C., buffered with 50 mM PBS ($Na_2HPO_4$—$NaH_2PO_4$, pH7.5).

It should be noted that the reaction can be carried out in a wide range of conditions, such as PBS 10-200 mM, eugenol concentration 0.1-2.0% (v/v), pH 4.5-9.0, and temperature 20-30° C.

In a preferred embodiment, the recombinant *E. coli* is cultured and the enzyme is expressed with TB medium.

The present invention provides a method for high-efficiency production of pinoresinol by use of an $H_2O_2$ auto-scavenging cascade. The advantages of the present method include usage of inexpensive and industrially available substrate, $H_2O_2$ auto-scavenging, highly efficient intermediate transportation, sustainable cofactor regeneration, and increased stability of the enzymes.

EXAMPLES

Figure 1:
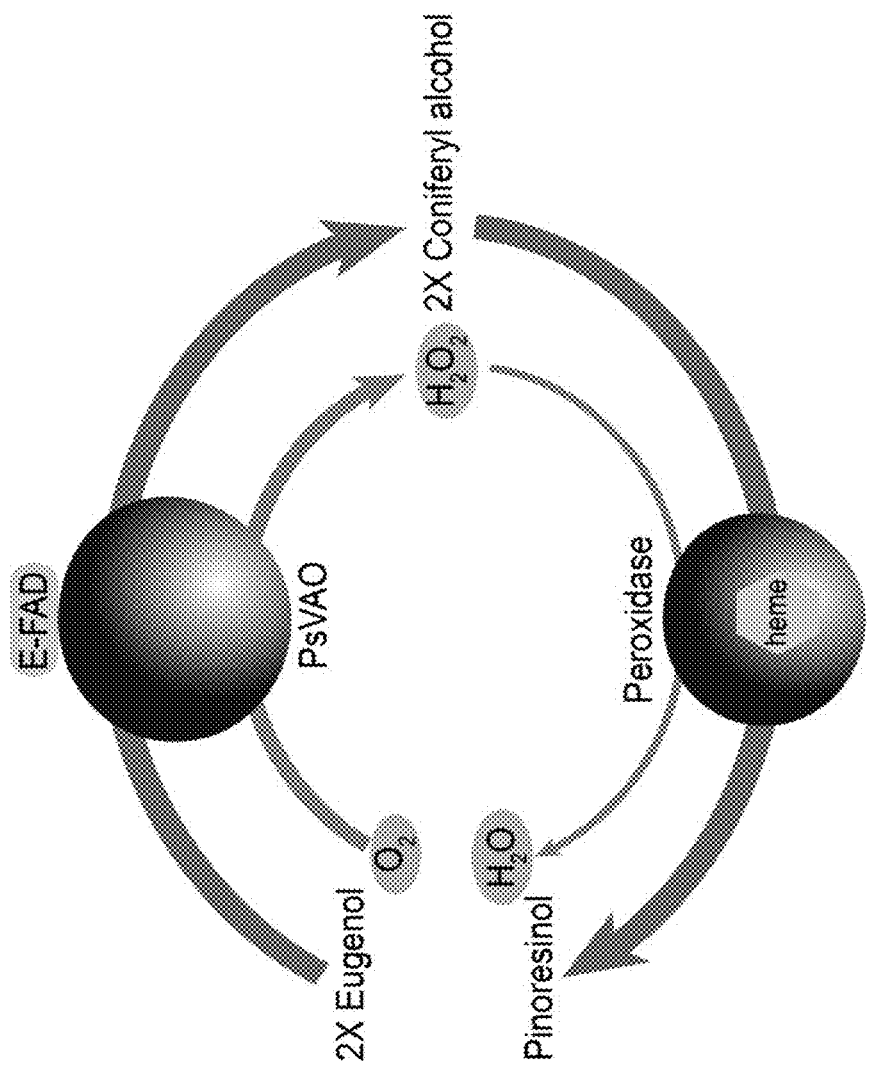
FIG. 1. Schematic mechanism of the pinoresinol production and $H_2O_2$ auto-scavenging cascade.

Materials and Methods:
Materials:
Pinoresinol and coniferyl alcohol were purchased from Sigma-Aldrich (St. Louis, Mo.). Gibson Assembly Master Mix kit was purchased from New England Biolabs, Inc (NEB, Ipswich, Mass.). Hydrogen peroxide assay kit and enhanced BCA protein assay kit were purchased from Beyotime biotechnology (Changzhou, China). *Penicillium simplicissimum* vanillyl alcohol oxidase gene (PsVAO) was optimized and synthesized by GenScript corporation (Nanjing, China).

Tb Medium:
yeast extract 24 g/L, tryptone 12 g/L, glycerol 4 mL/L, $KH_2PO_4$ 17 mM, $K_2HPO_4$ 72 mM. $KH_2PO_4/K_2HPO_4$ was sterilized by filtration and added to the medium before use. The rest was sterilized by autoclave.

PBS:
Prepare 50 mM $NaH_2PO_4$ and 50 mM $Na_2HPO_4$ respectively. Adjust $Na_2HPO_4$ to respective pH with $NaH_2PO_4$.

Sample Analysis:
One mL sample was drawn from the reaction system after it was mixed thoroughly. The samples were diluted 100 times with methanol, and mixed thoroughly for 1 min with a mixer. The samples were ionized with 1% (v/v) triethylamine after centrifugation at 12 000 rpm for 2 min and filtration with a 0.22 μm membrane. The samples were analyzed with Shimadzu LC-MS/MS-IT-TOF. Ten μL sample was injected with an autosampler. The flow phase A was 0.5% (v/v) triethylamine in $H_2O$; the flow phase B was methanol. The flow rate was 0.2 mL/min. The gradient was as follows: 0 min 40% B, 7 min 80% B, 11 min 40% B. Maintain 40% B for an additional 4 min. UV detector was used. Wavelength of 262 nm and 280 nm were used for the detection of pinoresinol and coniferyl alcohol, respectively. C18 reverse UPLC column Shimadzu Shim-pack VP-ODS (250 L×2.0) was used for the sample separation. Oven temperature was set 40° C. The negative ESI mode was used. The conditions were as follows: high voltage probe, −3.5 kV; nebulizing gas flow, 1.5 L/min; CDL temperature, 40° C.; heat block temperature, 200° C.; drying gas pressure, 200 KPa. Ar gas was used for CID. Detector voltage of TOF was 1.6 kV. m/z 50-600 [M-H]⁻ was collected for analysis. Gathering time was 10.00 msec. Repeat times was 3. Different concentrations of silybin, coniferyl alcohol and taxifolin standard were made for the quantitative analysis. The quantitative analysis was performed according to the UPLC peak areas.

Cell Growth and $H_2O_2$ Assay:
After pre-culturing in LB medium at 37° C. with shaking at 220 rpm overnight, recombinant strains were inoculated into 25 mL TB medium to a final concentration of 1% (v/v) in a 250 mL shaking flask. A final concentration of 50 mg/L kanamycin were added. Recombinant strains were cultured at 37° C. with shaking at 220 rpm until an $OD_{600}$ of 0.8, transferred to 25° C., and IPTG was added to a final concentration of 500 μM after precooling at 25° C. for 30 min. Protein expression was carried out at 25° C. with shaking at 220 rpm. Samples were removed at the time intervals indicated and used for measuring $OD_{600}$ values and intracellular $H_2O_2$. Cells were harvested by centrifugation at 9000 g, 4° C. for 2 min, resuspended in the same volume of precooled deionized water, and placed on ice. Intracellular $H_2O_2$ was released by sonicating on ice, measured using a hydrogen peroxide assay kit (Beyotime Biotechnology, Nantong, China), and normalized against the cytoplasmic volume using a standard ratio of 0.47 μL of internal volume per 1 mL of a culture of *E. coli* with $OD_{600}$ of 1.0.

Bioconversion:
After activation in LB medium at 37° C. with shaking at 220 rpm overnight, recombinant strains were inoculated into 25 mL TB medium to 1% (v/v) in a 250 mL shaking flask. A final concentration of 50 mg/L kanamycin were added. Recombinant strains were cultured at 37° C. with shaking at 220 rpm until logarithmic phase. Cultures were precooled to 25° C. and protein expression was induced by adding IPTG to a final concentration of 500 μM. After cultivation at 25° C. with shaking at 220 rpm for an additional 10 h, recombinant cells were collected by centrifugation at 4° C., 4000 g for 5 min. Cells were resuspended in PBS (50 mM, pH 7.0) after washing with PBS once, and adjusted to an $OD_{600}$ of 18. Bioconversion was carried out at 25° C. with shaking at 220 rpm, with 0.5% eugenol. Samples were removed at the indicated time intervals and used for the measurement of pinoresinol, coniferyl alcohol and intracellular $H_2O_2$. Intracellular $H_2O_2$ accumulated during the bioconversion was measured as described above.

Optimization:
Single factor optimizations of pH, temperature, rotation rate, and substrate concentration were carried out stepwise. Eugenol (0.5%, v/v) was emulsified in PBS (50 mM, pH 7.0)

using a high shear dispersing emulsifier and 1% (v/v) Tween-80. Different reaction media were tested at 20° C., 100 rpm, and 0.5% eugenol. In the feeding bioconversion, 0.2% or 0.5% eugenol was fed in each addition at 0, 1, 2, 3, 4, 5, 7, and 9 hr. Reactions were carried out in PBS (50 mM, pH 7.0) at 20° C., 100 rpm.

Scale-Up:

The reaction was scaled up to 1.5 L in a 3 L fermentor (T&J Bio-engineering Co. LTD, Shanghai, China). A pre-culture was grown in LB medium overnight, and 100 mL of culture was used to inoculate 1.5 L TB medium. Cells were cultured at 37° C., 700 rpm, and 4.5 sL/min until the $OD_{600}$ reached 9.5. The culture was then precooled to 25° C., and IPTG was added to a final concentration of 500 μM. Cells were then cultured for an additional 12 hr at 25° C. A final concentration of 0.2% (v/v) eugenol was added to start the reaction, which was carried out at 20° C., 200 rpm, and 1.0 sL/min. Thereafter, 0.15% (v/v) eugenol was added every 1 hr. As a result, a total amount of 1.85% (v/v, or 19.61 g/L) eugenol was added. Samples were collected every 1 hr before feeding and used for analysis. The dissolved oxygen (DO) at 0 hr was set at 100%.

Example 1: Construction of Recombinant Strains Harboring Different Genetic Architectures (I) Construction of PsVAO and Prx02 Co-Expressing Strains The peroxidase gene Prx02 was amplified from the genome DNA of *E. coli* BL21 (DE3) with primer pair SEQ ID NO:16/SEQ ID NO:17. The PCR product was separated with agarose gel. A 0.9 kb fragment was purified and subcloned into pMD 19 T Simple vector. The sequence was verified by Sanger sequencing. The nucleic acid sequence of Prx02 and coding amino acid sequence was SEQ ID NO:4 and SEQ ID NO:3. The verified Prx02 was subcloned into a ePathBrick vector pET-28a(PB) by Bam HI/Hind III resulting in recombinant plasmid pET-Prx02.

Figure 2:
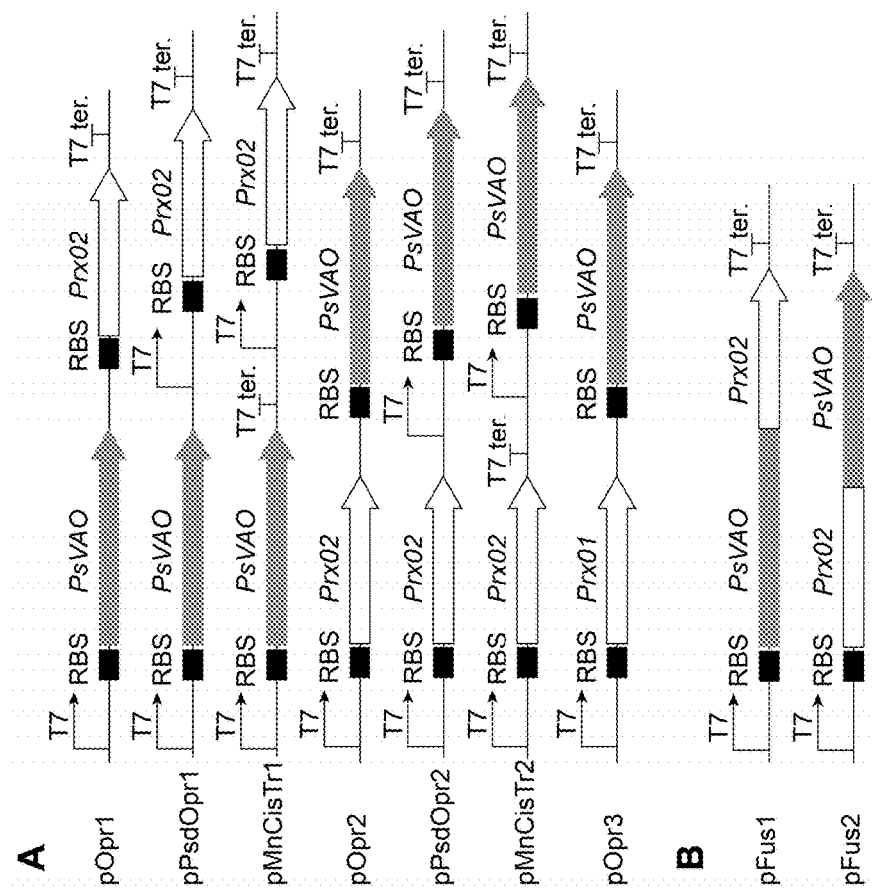
FIG. 2. Genetic architecture the enzymatic cascades. (A) Genetic structures constructed by ePathBrick approach. (B) Genetic structure constructed by fusion protein.

The *Penicillium simplicissimum* vanillyl alcohol oxidase gene PsVAO was optimized, synthesized, and subcloned into pUC57-Simple by GenScript corporation (Nanjing, China). The amino acid sequence and optimized nucleic acid sequence was SEQ ID NO:1 and SEQ ID NO:2 respectively. PsVAO was subcloned into a ePathBrick vector pET-28a (PB) by Bam HI/Hind III resulting in pET-PsVAO. Different co-expressing architectures, operon, pseudoperon, and monocistron were constructed by different isocaudamer pairs listed in Table 1. The resulting genetic architectures were shown in FIG. 2A.

(II) Construction of Plasmid Carrying Fusion Genes PsVAO-Prx02 and Prx02-PsVAO

Genes PsVAO and Prx02 were amplified with primer pairs SEQ ID NO:6/SEQ ID NO:7 and SEQ ID NO:8/SEQ ID NO:9, respectively. Plasmid backbone was amplified with primer pair SEQ ID NO:10/SEQ ID NO:11 from pUC18. PCR products were separated with agarose gel and purified with gel extraction kit. Recombinant plasmid pUC18-PsVAO-Prx02 was constructed with Gibson Assembly kit according to the manufacturer's guide. Genes Prx02 and PsVAO were amplified with primer pairs SEQ ID NO:12/SEQ ID NO:13 and SEQ ID NO:14/SEQ ID NO:15, respectively. Plasmid backbone was amplified with primer pair SEQ ID NO:10/SEQ ID NO:11 from pUC18. PCR products were separated with agarose gel and purified with gel extraction kit. Recombinant plasmid pUC18-Prx02-PsVAO was constructed with Gibson Assembly kit according to the manufacturer's guide. PsVAO and Prx02 were linked with a widely used linker GGGS in both recombinant plasmids. Restriction sites Bam HI/Hind III were used to digest pUC18-PsVAO-Prx02, pUC18-Prx02-PsVAO, and pET-28a(PB). The products were separated with agarose gel, and fragments of 2860 bp (PsVAO-Prx02 and Prx02-PsVAO) and 5346 bp (pET-28a(PB)) were purified with gel extraction kit. The fragments were linked with T4 ligase resulting in recombinant plasmids pFus1 and pFus2, respectively. The architectures of the plasmid were shown in FIG. 2B.

The plasmids co-expressing PsVAO and Prx02 or carrying fusion genes were transformed into *E. coli* BL21 (DE3) respectively, and resulted in recombinant strains with different genetic characteristics. As shown in Table 2.

Example 2. Analysis of Pinoresinol Production Using Different Enzymatic Cascades The recombinant strains were precultured in LB medium containing 50 mg/L kanamycin at 37° C., 220 rpm overnight. The strains were inoculated into 25 mL TB medium in 250 mL shaking flasks with an amount of 1% (v/v). A final concentration of 50 μg/mL kanamycin was added for the maintenance of plasmid. After incubation at 37° C., 220 rpm for 2 hr, the cultures were precooled at 25° C., 220 rpm for 30 min A final concentration of 500 μM IPTG was added for the induction of protein expression. The strains were cultured at 25° C., 220 rpm for an additional 10 hr. Cells were harvested by centrifugation at 5000 rpm, 4° C. for 5 min, washed with 50 mM PBS (pH7.0) and re-suspended in 50 mM PBS (pH7.0). The concentration of the cell was adjusted to $OD_{600}=18\pm1$, and 0.5% (v/v) eugenol was added as the substrate. The reaction was carried out in 250 mL shaking flask at 25° C., 220 rpm for 6 hr.

Figure 5:
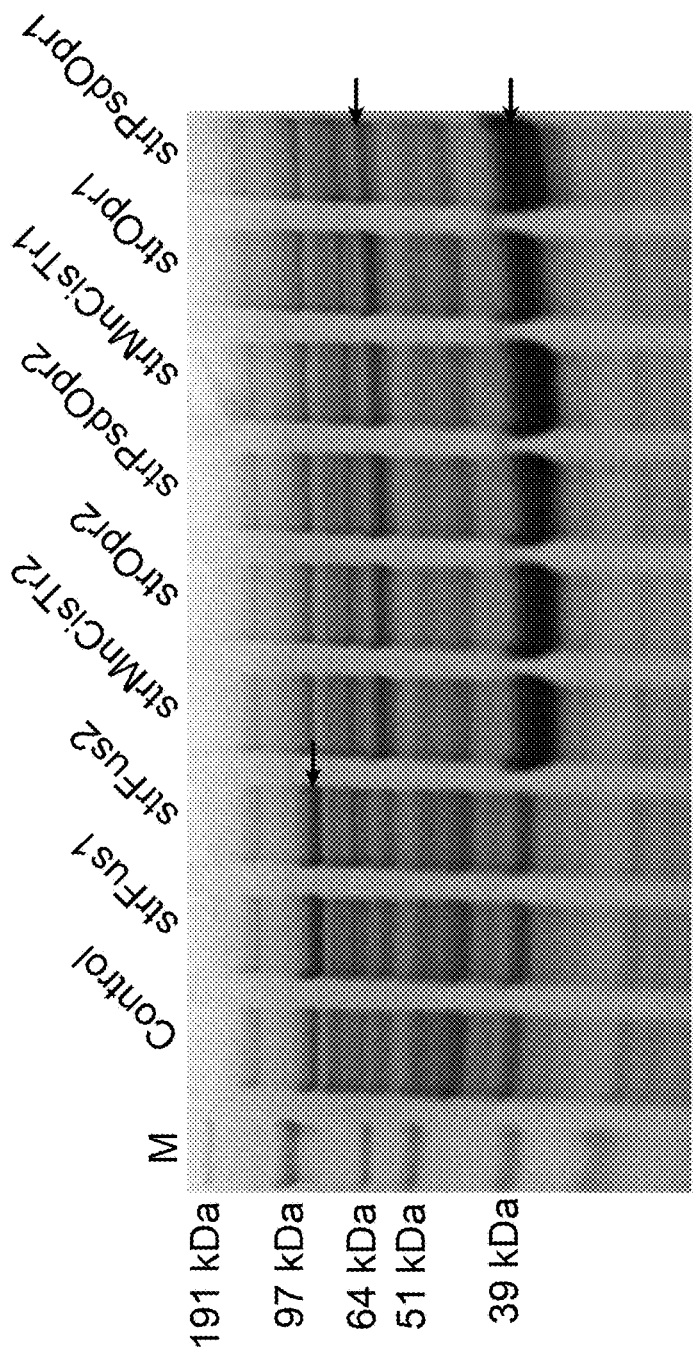
FIG. 5. Expression analysis of the enzymes by SDS-PAGE. Upper arrows refer to the fusion proteins PsVAO-Prx02 or Prx02-PsVAO. The middle arrows refer to PsVAO. The lower arrows refer to Prx02.

The expression of the enzymes was analyzed with SDS-PAGE. The cells were broken by ultrasound, and the supernatant was collected by centrifugation at 12000 rpm for 2 min and used for protein concentration determination and expression analysis. BCA protein analysis kit was used for protein concentration determination. *E. coli* BL21 (DE3) harboring pET-28a(PB) was used as blank control. Equal amount of protein samples were loaded for comparison. As shown in FIG. 5, both PsVAO and Prx02 were expressed in soluble forms in all co-expressing strains, and the fusion proteins PsVAO-Prx02 and Prx02-PsVAO were also expressed in soluble form in strains strFus1 and strFus2 respectively.

Figure 3:
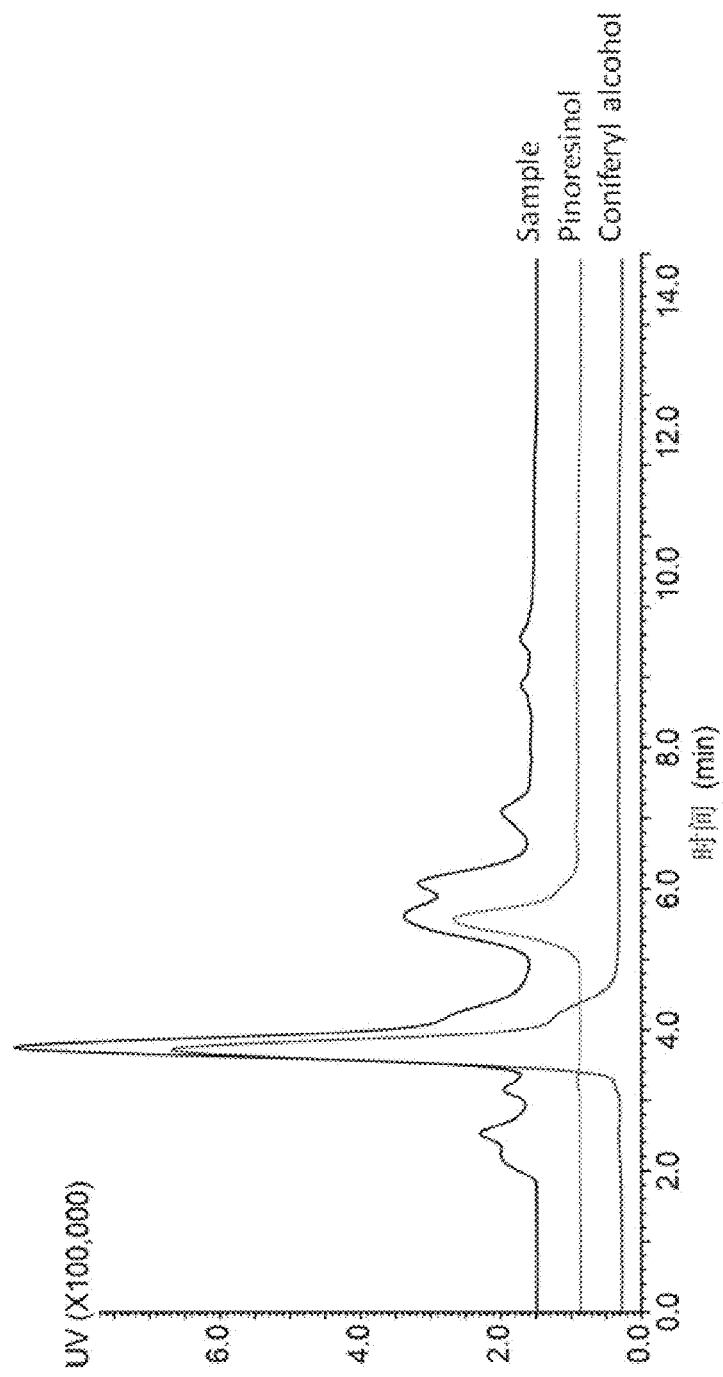
FIG. 3. UPLC spectrum of the samples.
Figure 4:
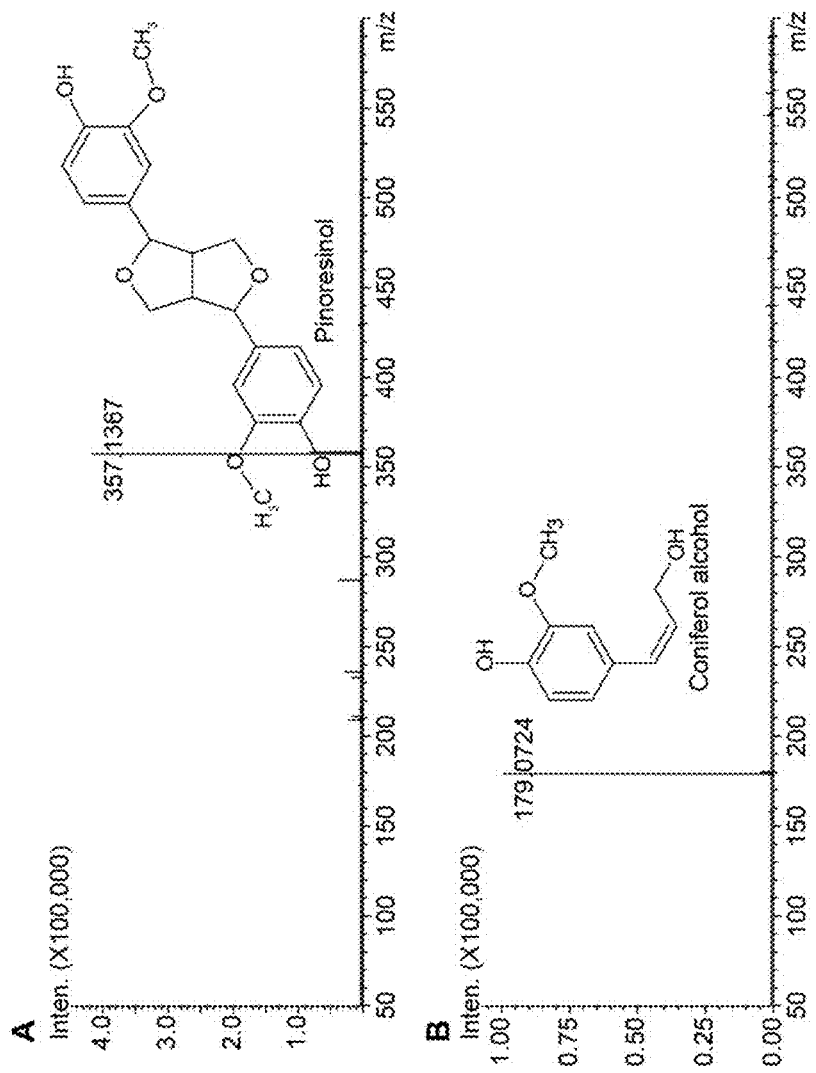
FIG. 4. Mass spectrum of pinoresinol (A) and coniferyl alcohol (B) under negative mode.

Analysis of the samples was performed with Shimadzu LC-MS/MS-IT-TOF. Negative mode was used for the determination of pinoresinol and coniferyl alcohol. The retention time of coniferyl alcohol and pinoresinol was 3.72 min and 5.56 min respectively (FIG. 3). m/z of coniferyl alcohol and pinoresinol in negative mode was 179.0724 and 357.1367 respectively (FIG. 4).

Figure 6:
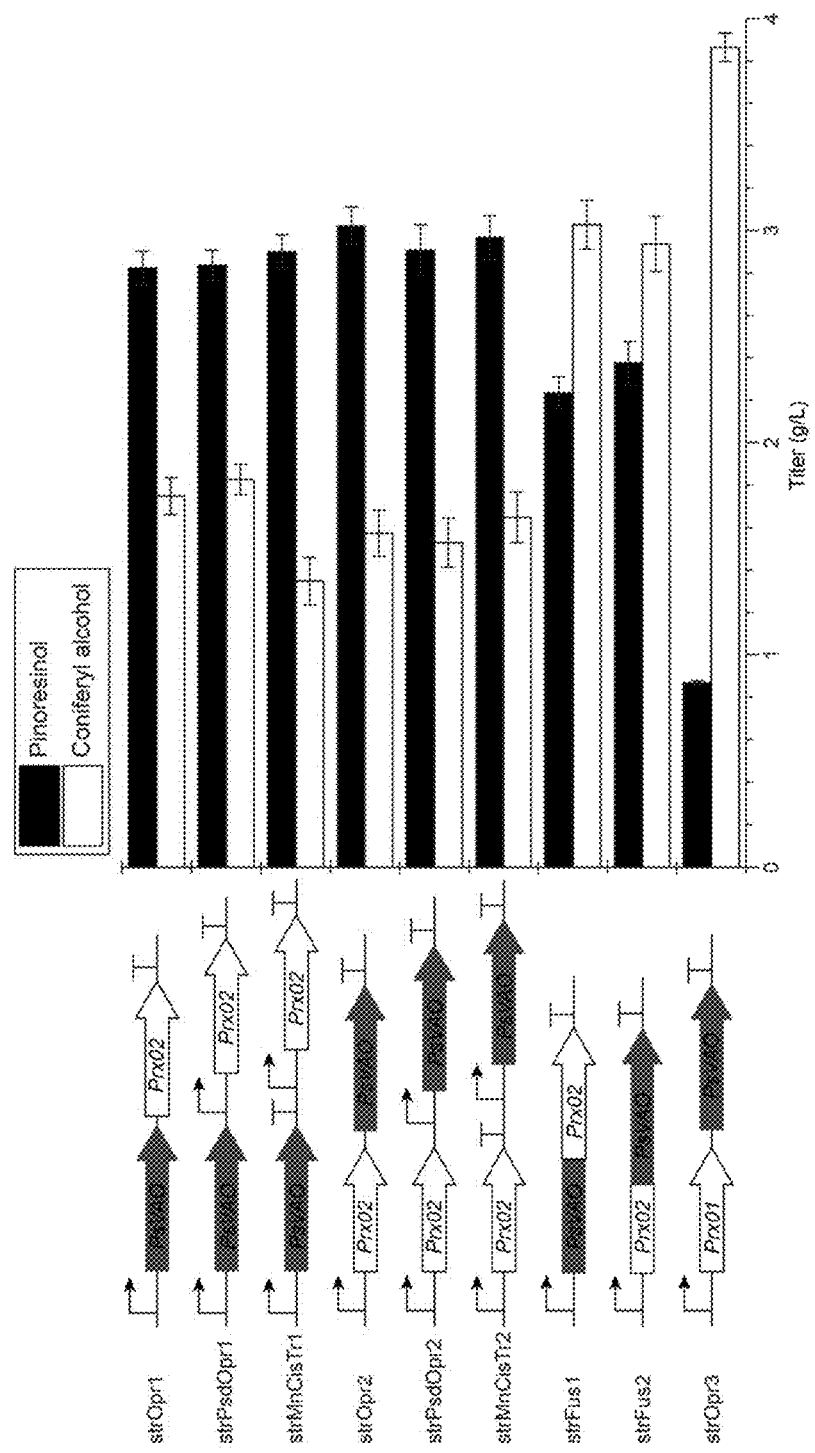
FIG. 6. Pinoresinol and coniferyl alcohol titer using different enzymatic cascades.

The titers of pinoresinol and coniferyl alcohol were analyzed according to the UPLC peak area, and shown as FIG. 6. The titer of pinoresinol and coniferyl alcohol differed notably among the strains. The strain strOpr2 showed highest pinoresinol titer of 3.02±0.09 g/L with an molar yield of 52.22%. This strain accumulated 1.57±0.11 g/L coniferyl alcohol. The titer of pinoresinol was negatively correlated with coniferyl alcohol, which demonstrated the activity of Prx02 was the limiting factor in the cascade. The strains strFus1 and strFus2 produced less pinoresinol whilst accumulated more coniferyl alcohol when compared with other strains. This can be a result of steric hinder effect to Prx02, despite the existence of the linker GGGS. It should be noted that the results were obtained before optimization. It was still higher than the highest titer (1.6 g/L) and molar yield (21%) ever reported. The strain strOpr2, which showed the highest titer and molar yield, was used in the following experiments.

Figure 7:
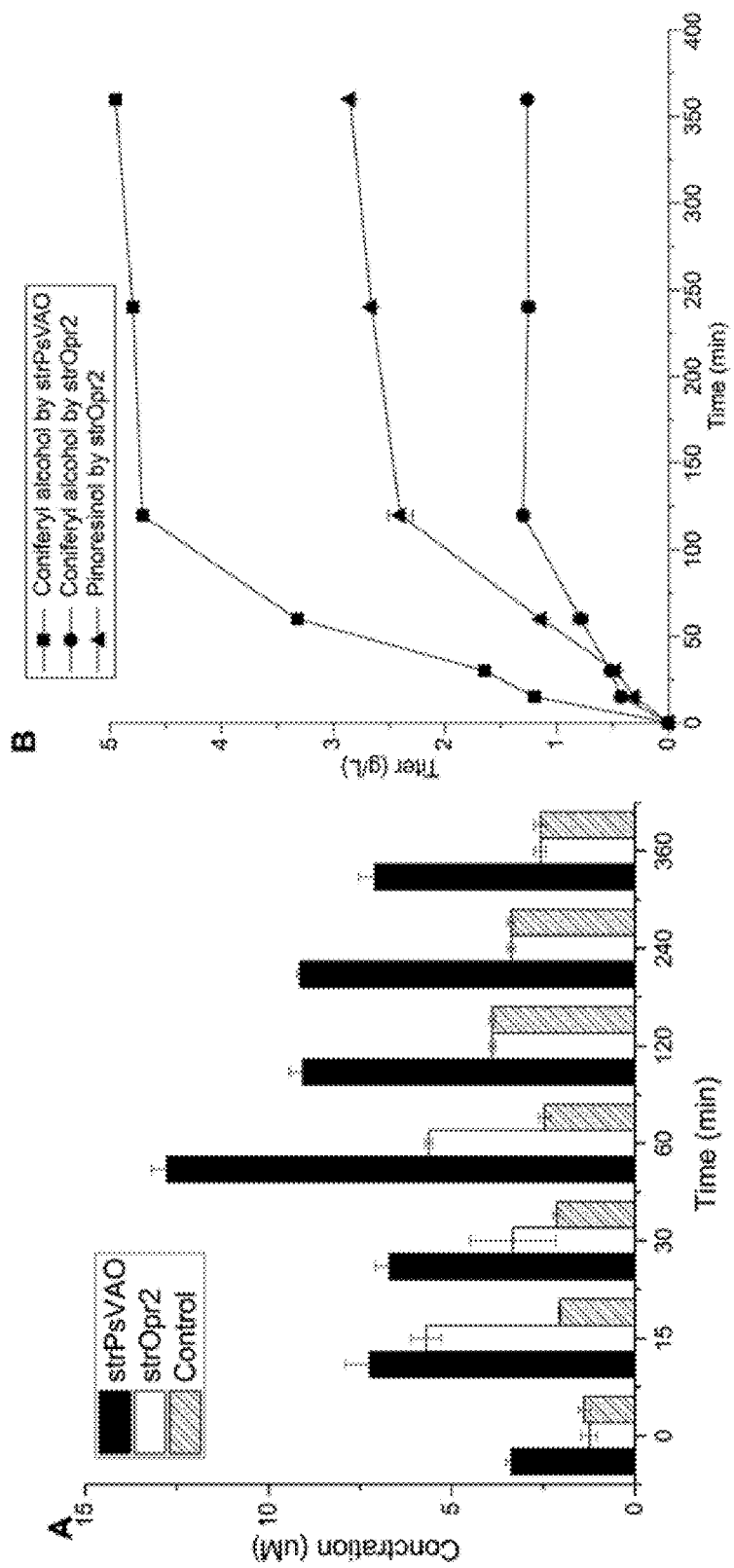
FIG. 7. Effect of $H_2O_2$ auto-scavenging cascade on intracellular $H_2O_2$ level during bioconversion. (A) Time course of $H_2O_2$ level of different strains during bioconversion. (B) Time course of pinoresinol and/or coniferyl alcohol production by different strains during the bioconversion.

Example 3: The Effect of $H_2O_2$ Auto-Scavenging on Intracellular $H_2O_2$ and Cell Growth The oxidation of eugenol by PsVAO produces $H_2O_2$, and the excessive accumulation of $H_2O_2$ will in turn inhibit enzyme activity. The intracellular $H_2O_2$ concentration in strPsVAO and strOpr2 was determined and compared with that of E. coli BL21 (DE3) harboring a blank pET-28a(PB) plasmid as a control. The results showed that the intracellular $H_2O_2$ concentration in both strPsVAO and strOpr2 increased after the bioconversion was initiated (FIG. 7A). In strOpr2, the concentration dropped to a level comparable with controls after 120 min, but the decrease was much slower in strPsVAO, and the intracellular $H_2O_2$ concentration remained higher than in strOpr2 throughout the reaction. These results clearly demonstrated that the $H_2O_2$ auto-scavenging cascade was effective for lowering intracellular $H_2O_2$ generated during the reaction. The titer of pinoresinol and coniferyl alcohol was also determined, and intracellular $H_2O_2$ levels were correlated with the rate of coniferyl alcohol production (FIG. 7B), which as described above is an $H_2O_2$-generating process.

Figure 8:
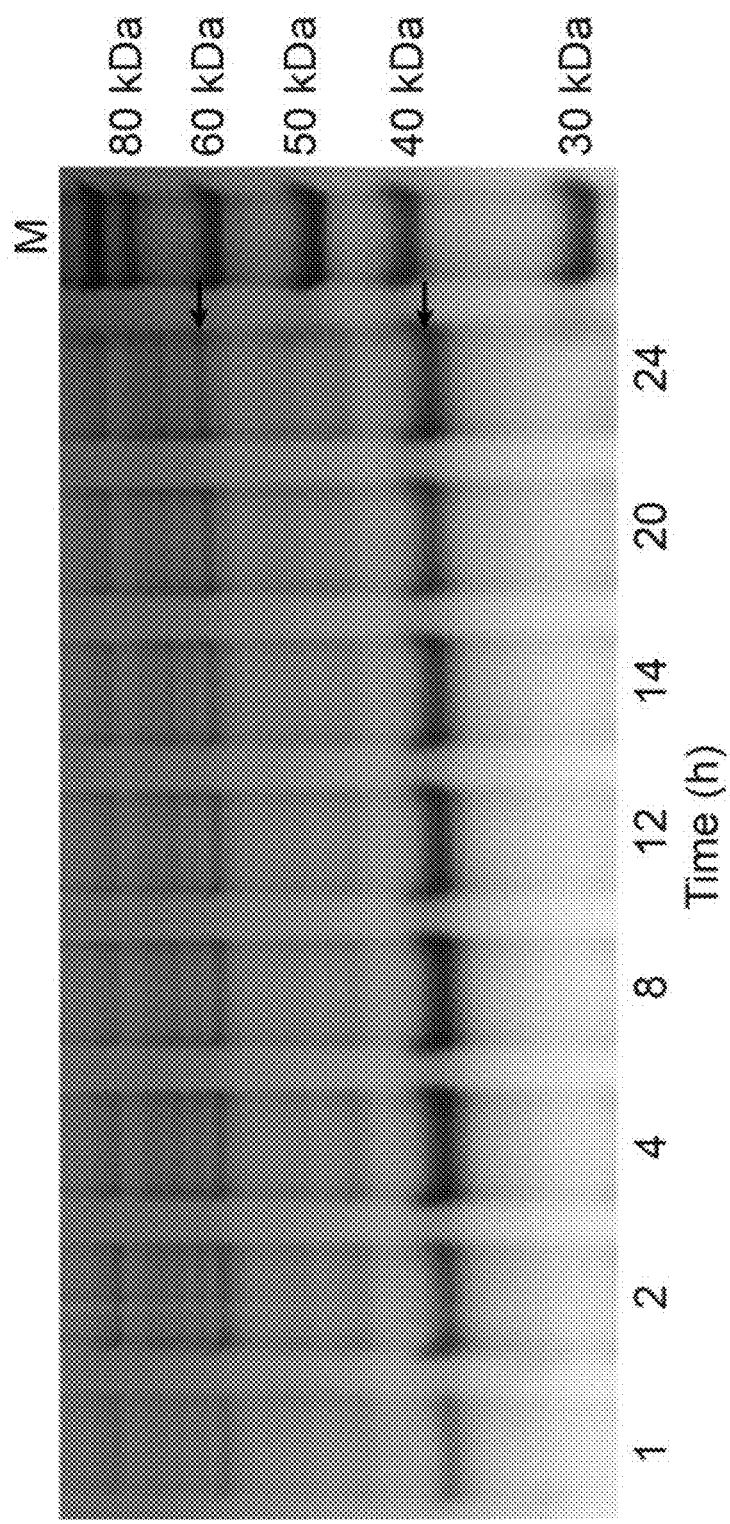
FIG. 8. Time course of PsVAO expression level after IPTG induction.
Figure 9:
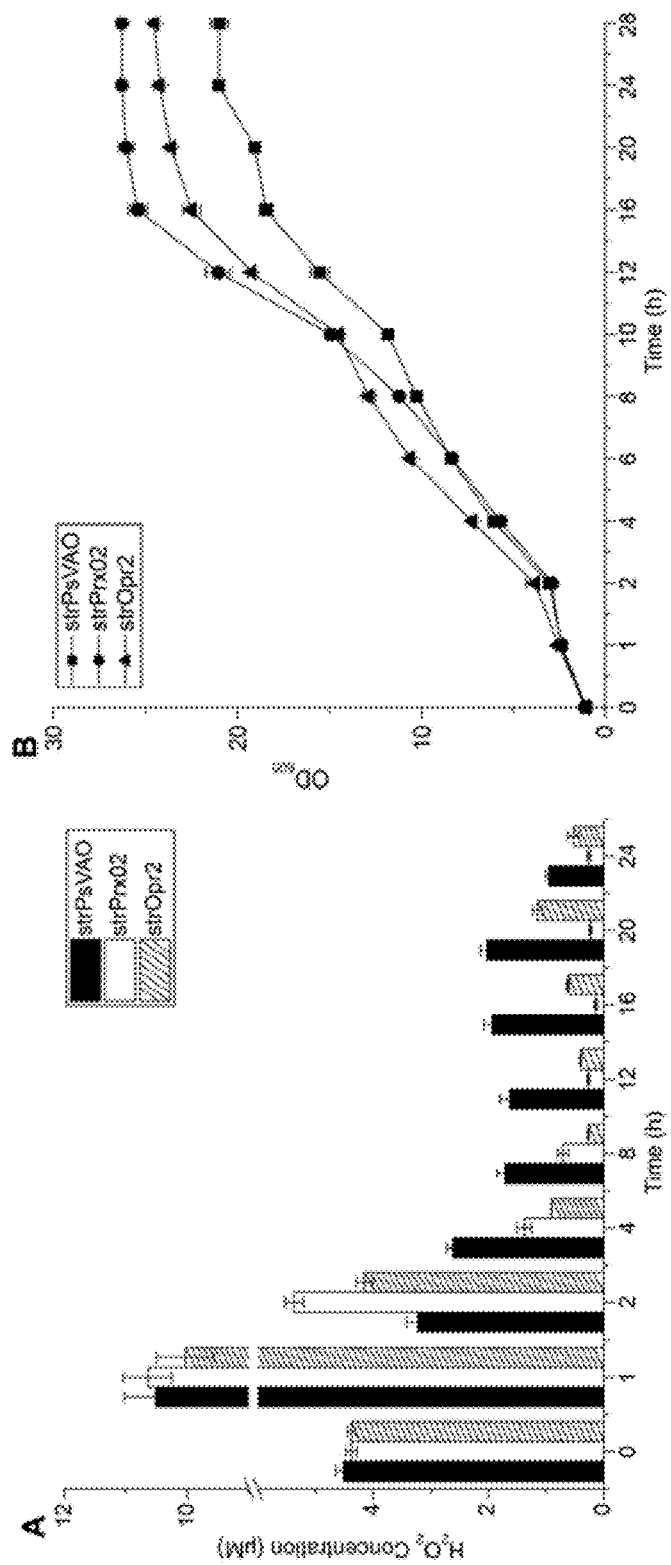
FIG. 9. Effect of $H_2O_2$ auto-scavenging cascade on intracellular $H_2O_2$ level and cell growth after IPTG induction. (A) Time course of $H_2O_2$ level of different strains after IPTG induction. (B) Time course of OD600 of different strains after IPTG induction.

In addition to the oxidation of aromatic alcohols, the versatile VAO also catalyzes demethylation, deamination, and hydroxylation reactions, all of which use oxygen as an electron acceptor and produce $H_2O_2$. The expression of PsVAO began at 1 hr after IPTG induction (FIG. 8). The function of the host cell may be impacted severely by excessive accumulation of $H_2O_2$ produced by the expressed PsVAO. Intracellular $H_2O_2$ and cell growth were therefore measured, and the results showed that in the first 2 hr after IPTG induction, a large amount of $H_2O_2$ was produced, and all strains accumulated a similar amount of intracellular $H_2O_2$. However, the $H_2O_2$ scavenging capability of strain strPsVAO was much weaker than the other two strains, and most efficient in the strPrx02 strain, as determined from the intracellular $H_2O_2$ concentration (FIG. 9A). Additionally, the final biomass was positively correlated with the $H_2O_2$ scavenging capability (FIG. 9B). This result is of great significance because the amount of recombinant enzyme is dependent on the status of the host cell, which must be robust and able to maintain intracellular homeostasis to support intracellular enzyme synthesis.

Example 4: Optimization and Scale-Up of the Bioconversion

Figure 10:
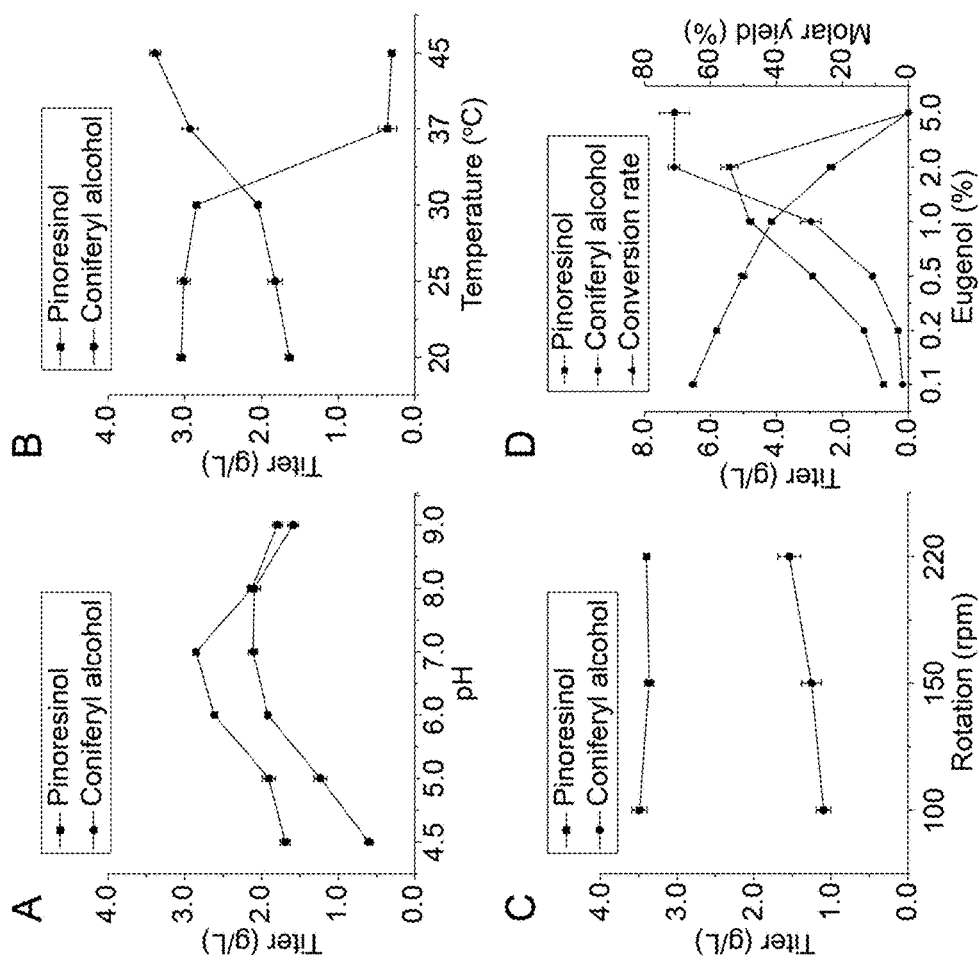
FIG. 10. Optimization of bioconversion conditions. (A) Optimization of pH. (B) Optimization of temperature. (C) Optimization of rotation rate. (D) Optimization of eugenol concentration.

The optimal pH and temperature can differ widely among enzymes, and these factors were optimized to balance the flux from eugenol to pinoresinol. The results showed that the optimal pH was 7.0 (FIG. 10A). Temperature was found to be an essential factor for pinoresinol production, as shown in FIG. 10B. The pinoresinol titer decreased slightly when the temperature was increased from 20° C. to 30° C., but it decreased dramatically when the temperature was increased to 37° C., from 2.85 g/L to 0.36 g/L, and the accumulation of coniferyl alcohol increased from 2.05 g/L to 2.93 g/L. This indicated that higher temperatures inhibited the activity of Prx02 but not PsVAO. Because the first step of the cascade is an $O_2$ consuming reaction, dissolved $O_2$ is a key factor. The results (FIG. 10C) showed that the pinoresinol titer decreased with increasing rotation rate (i.e. aeration), whereas the accumulation of coniferyl alcohol increased with increasing dissolved $O_2$. This indicated that a lower coniferyl alcohol accumulation rate helps to balance the flux to pinoresinol. The eugenol concentration was also determined due to its known toxic effects on host cells and enzymes. The titer of pinoresinol and coniferyl alcohol increased with increasing eugenol concentration from 0.1% to 2.0% (v/v) (FIG. 10D). The highest pinoresinol titer was 5.42 g/L when 2.0% (v/v) eugenol was used. When eugenol reached 5.0% (v/v), there was no pinoresinol detectable, and 7.10 g/L coniferyl alcohol accumulated. This indicated that 5.0% (v/v) eugenol totally abolished the activity of Prx02, but not PsVAO. The molar yield of pinoresinol decreased from 65.37% to 0% when the concentration of eugenol was increased from 0.1% to 5.0% (FIG. 10D). Based on these observations, pH 7.0, 20° C., and 100 rpm was used in subsequent bioconversions. Moreover, a low temperature and rotation rate saves energy and is thus more environmentally friendly, and less expensive.

Figure 11:
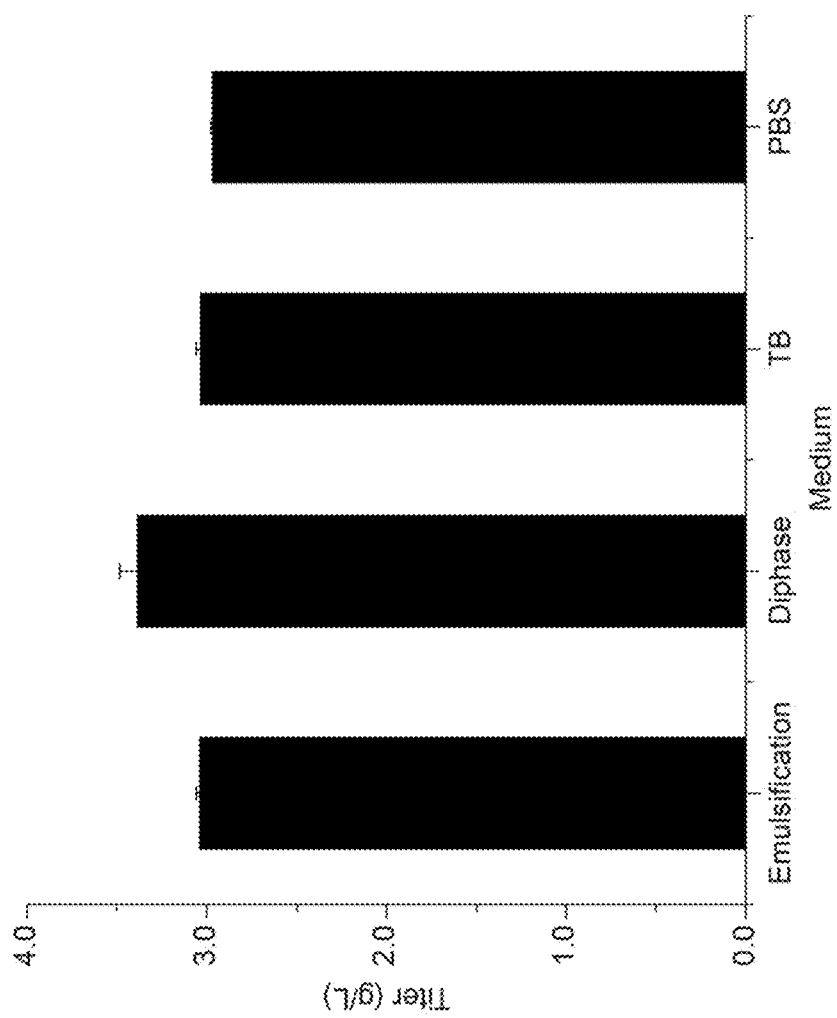
FIG. 11. Comparison of pinoresinol production of different bioconversion media.

Different culture media were also tested (FIG. 11). A biphasic medium composed of 80% (v/v) PBS and 20% ethyl acetate produced the highest amount of pinoresinol (3.38 g/L). The emulsification of eugenol in PBS did not have a noticeable effect on the titer. Additionally, the use of TB medium eliminated the need for harvesting and transferring cells from TB medium to PBS. This is of great significance for industrial applications because the separation of cells from the fermentation broth is not easy at an industrial scale. As shown in FIG. 11, the use of TB medium did not have a notable effect on the pinoresinol titer compared with PBS.

Figure 12:
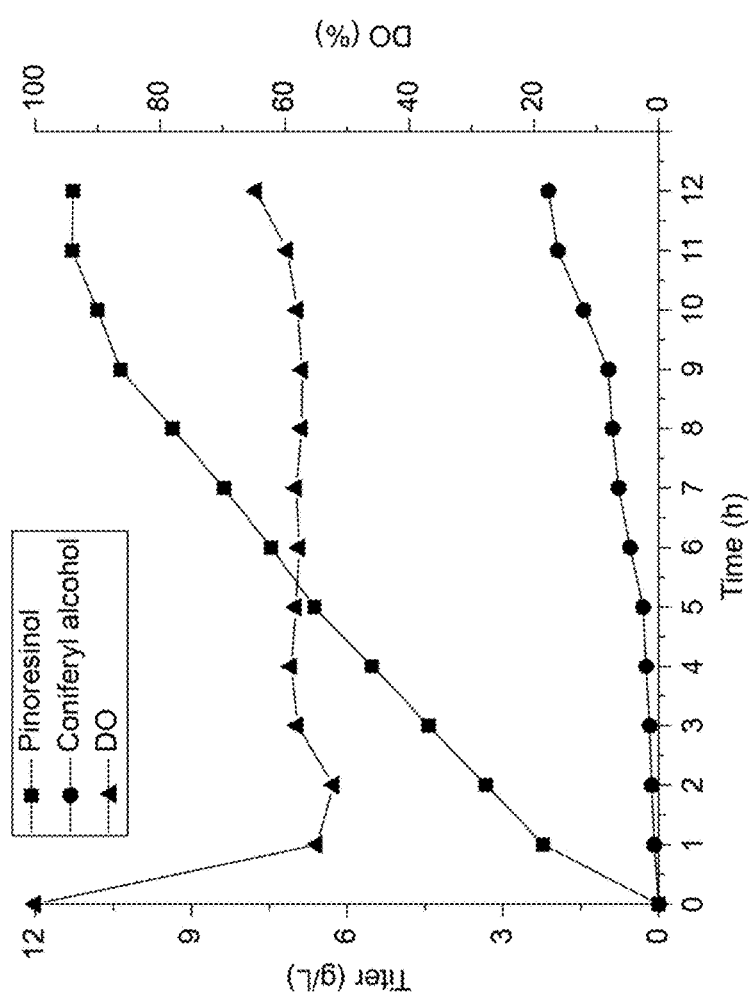
FIG. 12. Time course of coniferyl alcohol and pinoresinol titer and $OD_{600}$.

Scale-up of the reaction was carried out in 1.5 L TB medium in a 3 L fermentor. A strOpr2 culture with an optical density ($OD_{600}$) of 39.31 was used as the catalyst. The reaction was started by adding 0.2% (v/v) eugenol. By feeding 0.15% (v/v) eugenol at each addition, eugenol levels remained below detectable levels, and the maximum titer of pinoresinol (11.29 g/L) was reached after 11 hr, with a molar yield of 52.77% (FIG. 12). The theoretical productivity was calculated to be 1.03 g/(L·h). This is the highest titer, yield and productivity ever reported. The coniferyl alcohol level remained below 2.0 g/L over the first 11 hr. This indicated that feeding eugenol continuously and keeping it at a low level alleviated enzyme inhibition. As described above, the reaction consumes oxygen, and the dissolved oxygen (DO) content decreased quickly to around 60% shortly after the start of the reaction (FIG. 12). The DO decreased further to around 40% in 2 min after the feeding of eugenol, and recovered to 60% over the following 30 min (data not shown). This indicated that the oxidation of eugenol was complete in 30 min.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

TABLE 1

Combination of starting plasmids, restriction sites, and fragments and corresponding co-expressing plasmids

| Starting plasmid | Restriction site | Fragment (bp) | Co-expressing plasmid |
|---|---|---|---|
| pET-PsVAO | Spe I/Sal I | 6924 | pOpr1 |
| pET-Prx02 | Xba I/Sal I | 1211 | |
| pET-PsVAO | Spe I/Sal I | 6924 | pPsdOpr1 |
| pET-Prx02 | Avr II/Sal I | 1325 | |
| pET-PsVAO | Nhe I/Sal I | 7017 | pMnCisTr1 |
| pET-Prx02 | Avr II/Sal I | 1325 | |
| pET-Prx02 | Spe I/Sal I | 6143 | pOpr2 |
| pET-PsVAO | Xba I/Sal I | 1992 | |
| pET-Prx02 | Spe I/Sal I | 6143 | pPsdOpr2 |
| pET-PsVAO | Avr II/Sal I | 2106 | |
| pET-Prx02 | Nhe I/Sal I | 6236 | pMnCisTr2 |
| pET-PsVAO | Avr II/Sal I | 2106 | |

TABLE 2

Strains, genetic characteristics, and plasmid architectures

| Strains | Genetic characteristics | Plasmid architectures |
|---|---|---|
| strPsVAO | E. coli BL21 (DE3) harboring pET-PsVAO | pET-28a(PB) carrying PsVAO |
| strPrx02 | E. coli BL21 (DE3) harboring pET-Prx02 | pET-28a(PB) carrying Prx02 |
| strOpr1 | E. coli BL21 (DE3) harboring pOpr1 | pET-28a(PB) carrying PsVAO and Prx02 in operon form |
| strPsdOpr1 | E. coli BL21 (DE3) harboring pPsdOpr1 | pET-28a(PB) carrying PsVAO and Prx02 in pseudoperon form |
| strMnCisTr1 | E. coli BL21 (DE3) harboring pMnCisTr1 | pET-28a(PB) carrying PsVAO and Prx02 in monocistron form |
| strOpr2 | E. coli BL21 (DE3) harboring pOpr2 | pET-28a(PB) carrying Prx02 and PsVAO in operon form |
| strPsdOpr2 | E. coli BL21 (DE3) harboring pPsdOpr2 | pET-28a(PB) carrying Prx02 and PsVAO in pseudoperon form |
| strMnCisTr2 | E. coli BL21 (DE3) harboring pMnCisTr2 | pET-28a(PB) carrying Prx02 and PsVAO in monocistron form |
| strFus1 | E. coli BL21 (DE3) harboring pFus1 | pET-28a(PB) carrying fusion gene PsVAO-Prx02 |
| strFus2 | E. coli BL21 (DE3) harboring pFus2 | pET-28a(PB) carrying fusion gene Prx02-PsVAO |

REFERENCES

1. Xu P, Vansiri A, Bhan N, Koffas M A G. ePathBrick: A synthetic biology platform for engineering metabolic pathways in E. coli. *ACS Synth Biol* 1, 256-266 (2012).

What is claimed is:

1. A method for production of pinoresinol using an $H_2O_2$ auto-scavenging enzymatic cascade, wherein eugenol is used as a substrate and a whole-cell recombinant *Escherichia coli* is used as a catalyst to convert eugenol to pinoresinol, wherein the recombinant *Escherichia coli* over-expresses a vanillyl alcohol oxidase comprising the amino acid sequence of SEQ ID NO:1 and a peroxidase comprising the amino acid sequence of SEQ ID NO:3 or a fusion protein of the vanillyl alcohol oxidase and the peroxidase.

2. The method of claim 1, comprising the steps of:
   a) culturing the recombinant *Escherichia coli* and inducing over-expression of the vanillyl alcohol oxidase and the peroxidase or the fusion protein of the vanillyl alcohol oxidase and the peroxidase;
   b) incubating eugenol in the culture medium of the whole-cell recombinant *Escherichia coli*; and
   c) converting eugenol to pinoresinol by an enzymatic cascade with the vanillyl alcohol oxidase and the peroxidase.

3. The method of claim 2, wherein the culture medium for converting eugenol to pinoresinol comprises 10-200 mM PBS, the recombinant *Escherichia coli* cell with a concentration of $OD_{600}=18\pm1$, 0.1-2.0% (v/v) eugenol, pH 4.5-9.0, at 20-30° C.

4. The method of claim 2, wherein the culture medium for converting eugenol to pinoresinol comprises 50 mM PBS, the recombinant *Escherichia coli* cell with a concentration of $OD_{600}=18\pm1$, 0.5% (v/v) eugenol, pH 7.0, at 20° C.

5. The method of claim 1, wherein the recombinant *Escherichia coli* contains a strOpr2 construct that sequentially comprises a promoter, the VAO gene, the peroxidase gene, and a terminator.

* * * * *

```
SEQUENCE LISTING

<160> NUMBER OF SEQ ID NOS: 17

<210> SEQ ID NO 1
<211> LENGTH: 560
<212> TYPE: PRT
<213> ORGANISM: Penicillium simplicissimum

<400> SEQUENCE: 1

Met Ser Lys Thr Gln Glu Phe Arg Pro Leu Thr Leu Pro Pro Lys Leu
1               5                   10                  15

Ser Leu Ser Asp Phe Asn Glu Phe Ile Gln Asp Ile Ile Arg Ile Val
            20                  25                  30

Gly Ser Glu Asn Val Glu Val Ile Ser Ser Lys Asp Gln Ile Val Asp
        35                  40                  45

Gly Ser Tyr Met Lys Pro Thr His Thr His Asp Pro His His Val Met
    50                  55                  60

Asp Gln Asp Tyr Phe Leu Ala Ser Ala Ile Val Ala Pro Arg Asn Val
65                  70                  75                  80

Ala Asp Val Gln Ser Ile Val Gly Leu Ala Asn Lys Phe Ser Phe Pro
                85                  90                  95

Leu Trp Pro Ile Ser Ile Gly Arg Asn Ser Gly Tyr Gly Gly Ala Ala
                100                 105                 110

Pro Arg Val Ser Gly Ser Val Val Leu Asp Met Gly Lys Asn Met Asn
            115                 120                 125

Arg Val Leu Glu Val Asn Val Glu Gly Ala Tyr Cys Val Val Glu Pro
        130                 135                 140

Gly Val Thr Tyr His Asp Leu His His Asn Tyr Leu Glu Ala Asn Asn Leu
145                 150                 155                 160

Arg Asp Lys Leu Trp Leu Asp Val Pro Asp Leu Gly Gly Gly Ser Val
                165                 170                 175

Leu Gly Asn Ala Val Glu Arg Gly Val Gly Tyr Thr Pro Tyr Gly Asp
                180                 185                 190
```

```
His Trp Met Met His Ser Gly Met Glu Val Val Leu Ala Asn Gly Glu
        195                 200                 205

Leu Leu Arg Thr Gly Met Gly Ala Leu Pro Asp Pro Lys Arg Pro Glu
        210                 215                 220

Thr Met Gly Leu Lys Pro Glu Asp Gln Pro Trp Ser Lys Ile Ala His
225                 230                 235                 240

Leu Phe Pro Tyr Gly Phe Gly Pro Tyr Ile Asp Gly Leu Phe Ser Gln
                245                 250                 255

Ser Asn Met Gly Ile Val Thr Lys Ile Gly Ile Trp Leu Met Pro Asn
            260                 265                 270

Pro Gly Gly Tyr Gln Ser Tyr Leu Ile Thr Leu Pro Lys Asp Gly Asp
        275                 280                 285

Leu Lys Gln Ala Val Asp Ile Ile Arg Pro Leu Arg Leu Gly Met Ala
        290                 295                 300

Leu Gln Asn Val Pro Thr Ile Arg His Ile Leu Leu Asp Ala Ala Val
305                 310                 315                 320

Leu Gly Asp Lys Arg Ser Tyr Ser Ser Lys Thr Glu Pro Leu Ser Asp
                325                 330                 335

Glu Glu Leu Asp Lys Ile Ala Lys Gln Leu Asn Leu Gly Arg Trp Asn
            340                 345                 350

Phe Tyr Gly Ala Leu Tyr Gly Pro Glu Pro Ile Arg Arg Val Leu Trp
        355                 360                 365

Glu Thr Ile Lys Asp Ala Phe Ser Ala Ile Pro Gly Val Lys Phe Tyr
370                 375                 380

Phe Pro Glu Asp Thr Pro Glu Asn Ser Val Leu Arg Val Arg Asp Lys
385                 390                 395                 400

Thr Met Gln Gly Ile Pro Thr Tyr Asp Glu Leu Lys Trp Ile Asp Trp
                405                 410                 415

Leu Pro Asn Gly Ala His Leu Phe Phe Ser Pro Ile Ala Lys Val Ser
            420                 425                 430

Gly Glu Asp Ala Met Met Gln Tyr Ala Val Thr Lys Lys Arg Cys Gln
        435                 440                 445

Glu Ala Gly Leu Asp Phe Ile Gly Thr Phe Thr Val Gly Met Arg Glu
        450                 455                 460

Met His His Ile Val Cys Ile Val Phe Asn Lys Lys Asp Leu Ile Gln
465                 470                 475                 480

Lys Arg Lys Val Gln Trp Leu Met Arg Thr Leu Ile Asp Asp Cys Ala
                485                 490                 495

Ala Asn Gly Trp Gly Glu Tyr Arg Thr His Leu Ala Phe Met Asp Gln
            500                 505                 510

Ile Met Glu Thr Tyr Asn Trp Asn Asn Ser Ser Phe Leu Arg Phe Asn
        515                 520                 525

Glu Val Leu Lys Asn Ala Val Asp Pro Asn Gly Ile Ile Ala Pro Gly
530                 535                 540

Lys Ser Gly Val Trp Pro Ser Gln Tyr Ser His Val Thr Trp Lys Leu
545                 550                 555                 560

<210> SEQ ID NO 2
<211> LENGTH: 1683
<212> TYPE: DNA
<213> ORGANISM: Penicillium simplicissimum

<400> SEQUENCE: 2
atgagcaaaa cccaggaatt tcgtccgctg accctgccgc cgaaactgag tctgagcgat    60
```

-continued

```
ttcaacgagt tcatccagga catcatccgt atcgtgggta gcgaaaacgt cgaagtcatc    120
agcagcaaag atcagatcgt tgacggctct tacatgaaac cgacccatac ccacgatccg    180
caccacgtta tggatcagga ctacttcctg gcatctgcaa ttgttgcacc gcgtaacgtt    240
gcagatgttc aaagcattgt tggcctggca acaaattct cctttccgct gtggccgatc     300
agtattgggc gtaattctgg ttacggcggt gcagcaccgc gcgttagcgg tagcgttgtt    360
ctggatatgg gcaaaaacat gaaccgcgtc ctggaagtta acgtcgaagg cgcatattgc    420
gttgttgaac cgggcgttac ctatcacgat ctgcacaact acctggaagc gaataacctg    480
cgcgataaac tgtggctgga cgttccggat ctgggtggcg ttctgttcct gggtaacgca    540
gttgaacgtg gcgttggtta taccccgtac ggcgatcatt ggatgatgca tagcggtatg    600
gaggttgttc tggcaaacgg cgaactgctg cgtaccggta tgggcgcact gccggacccg    660
aaacgtccgg aaacgatggg cctgaaaccg gaagatcaac cgtggagcaa aatcgcgcac    720
ctgtttccgt acggttttgg tccgtacatc gacggtctgt tttcccagtc taacatgggt    780
atcgtcacca aaatcggcat ctggctgatg ccgaatccgg gcggttatca aagctatctg    840
atcaccctgc cgaaagacgg cgatctgaaa caggcggttg atattattcg tccgctgcgt    900
ctgggtatgg cactgcaaaa cgttccgacc attcgccata ttctgctgga cgcagcagtt    960
ctgggcgata acgtagcta cagcagcaaa accgaaccgc tgtctgacga agaactggac   1020
aaaatcgcga acagctgaa cctgggtcgt tggaatttt acggcgcact gtacggtccg    1080
gaaccgattc gtcgcgttct gtgggaaacc attaaagacg cgtttagcgc aattccgggc   1140
gtcaaattct acttcccgga agatacccg gaaaacagcg ttctgcgcgt tcgcgataaa    1200
accatgcagg gtattccgac ctacgacgaa ctgaaatgga ttgattggct gccgaacggc   1260
gcgcacctgt tcttcagccc gatcgcgaaa gtttctggcg aagacgcaat gatgcagtac   1320
gcggttacca aaaacgctg tcaggaagca ggcctggatt ttattggcac ctttaccgtc    1380
ggtatgcgcg aaatgcatca tatcgtctgc atcgtcttca acaaaaaga cctgatccag   1440
aaacgcaaag tccagtggct gatgcgtacc ctgattgacg attgcgcagc aaacggttgg   1500
ggcgaatatc gtacccatct ggcgtttatg gaccagatca tggagaccta caactggaac   1560
aacagcagct tcctgcgctt taacgaagtc ctgaaaaacg cggttgatcc gaacggtatc   1620
attgcaccgg taaatctgg cgtttggccg agtcagtata gccacgtcac ctggaaactg    1680
taa                                                                1683
```

<210> SEQ ID NO 3
<211> LENGTH: 299
<212> TYPE: PRT
<213> ORGANISM: Escherichia coli BL21 (DE3)

<400> SEQUENCE: 3

```
Met Ser Gln Val Gln Ser Gly Ile Leu Pro Glu His Cys Arg Ala Ala
1               5                   10                  15

Ile Trp Ile Glu Ala Asn Val Lys Gly Glu Val Asp Ala Leu Arg Ala
            20                  25                  30

Ala Ser Lys Thr Phe Ala Asp Lys Leu Ala Thr Phe Glu Ala Lys Phe
        35                  40                  45

Pro Asp Ala His Leu Gly Ala Val Val Ala Phe Gly Asn Asn Thr Trp
    50                  55                  60

Arg Ala Leu Ser Gly Gly Val Gly Ala Glu Glu Leu Lys Asp Phe Pro
65                  70                  75                  80
```

Gly Tyr Gly Lys Gly Leu Ala Pro Thr Thr Gln Phe Asp Val Leu Ile
            85                  90                  95

His Ile Leu Ser Leu Arg His Asp Val Asn Phe Ser Val Ala Gln Ala
            100                 105                 110

Ala Met Glu Ala Phe Gly Asp Cys Ile Glu Val Lys Glu Glu Ile His
        115                 120                 125

Gly Phe Arg Trp Val Glu Glu Arg Asp Leu Ser Gly Phe Val Asp Gly
    130                 135                 140

Thr Glu Asn Pro Ala Gly Glu Thr Arg Arg Glu Val Ala Val Ile
145                 150                 155                 160

Lys Asp Gly Val Asp Ala Gly Gly Ser Tyr Val Phe Val Gln Arg Trp
                165                 170                 175

Glu His Asn Leu Lys Gln Leu Asn Arg Met Ser Val His Asp Gln Glu
            180                 185                 190

Met Met Ile Gly Arg Thr Lys Glu Ala Asn Glu Glu Ile Asp Gly Asp
        195                 200                 205

Glu Arg Pro Glu Thr Ser His Leu Thr Arg Val Asp Leu Lys Glu Asp
    210                 215                 220

Gly Lys Gly Leu Lys Ile Val Arg Gln Ser Leu Pro Tyr Gly Thr Ala
225                 230                 235                 240

Ser Gly Thr His Gly Leu Tyr Phe Cys Ala Tyr Cys Arg Leu His
                245                 250                 255

Asn Ile Glu Gln Gln Leu Leu Ser Met Phe Gly Asp Thr Asp Gly Lys
            260                 265                 270

Arg Asp Ala Met Leu Arg Phe Thr Lys Pro Val Thr Gly Gly Tyr Tyr
        275                 280                 285

Phe Ala Pro Ser Leu Asp Lys Leu Met Ala Leu
    290                 295

<210> SEQ ID NO 4
<211> LENGTH: 900
<212> TYPE: DNA
<213> ORGANISM: Escherichia coli BL21 (DE3)

<400> SEQUENCE: 4

```
atgtctcagg ttcagagtgg cattttgcca gaacattgcc gcgcggcgat ttggatcgaa      60
gccaacgtga aagggaagt tgacgccctg cgtgcggcca gtaaaacatt tgccgacaaa     120
ctggcaactt ttgaagcgaa attcccggac gcgcatcttg gtgcggtggt tgcctttggt     180
aacaacacct ggcgcgctct gagcggcggc gttgggcag aagagctgaa agattttccg     240
ggctacggta aaggccttgc gccgaccacc cagttcgatg tgttgatcca cattctttct     300
ctgcgtcacg acgtaaactt ctctgtcgcc caggcggcga tggaagcctt ggtgactgc     360
attgaagtga agaagagat ccacggcttc cgttgggttg aagagcgtga cctgagcggc     420
tttgttgacg gtacggaaaa cccggcgggt gaagagacgc gtcgcgaagt ggcggttatc     480
aaagacggcg tggatgcggg cggcagctat gtgtttgtcc agcgttggga acacaacctg     540
aagcagctca accggatgag cgttcacgat caggagatga tgatcgggcg caccaaagag     600
gccaacgaag agatcgacgg cgacgaacgt ccggaaacct ctcacctcac cgcgttgat     660
ctgaaagaag atggcaaagg gctgaagatt gttcgccaga gctgccgta cggcactgcc     720
agtggcactc acggtctgta cttctgcgcc tactgcgcgc gtctgcataa cattgagcag     780
caactgctga gcatgtttgg cgataccgat ggtaagcgtg atgcgatgtt gcgtttcacc     840
```
aaaccggtaa ccggcggcta ttatttcgca ccgtcgctgg acaagttgat ggcgctgtaa    900

<210> SEQ ID NO 5
<211> LENGTH: 5371
<212> TYPE: DNA
<213> ORGANISM: Artificial Sequence
<220> FEATURE:
<223> OTHER INFORMATION: vector pET-28a(PB)

<400> SEQUENCE: 5
gccatattca acgggaaacg tcttgctcta ggccgcgatt aaattccaac atggatgctg     60
atttatatgg gtataaatgg gctcgcgata atgtcgggca atcaggtgcg acaatctatc    120
gattgtatgg gaagcccgat gcgccagagt tgtttctgaa acatggcaaa ggtagcgttg    180
ccaatgatgt tacagatgag atggtcagac taaactggct gacggaattt atgcctcttc    240
cgaccatcaa gcattttatc cgtactcctg atgatgcatg ttactcacc actgcgatcc     300 ccgggaaaac agcattccag gtattagaag aatatcctga ttcaggtgaa atatattgttg   360 atgcgctggc agtgttcctg cgccggttgc attcgattcc tgtttgtaat tgtccttta    420 acagcgatcg cgtatttcgt ctcgctcagg cgcaatcacg aatgaataac ggtttggttg    480
atgcgagtga ttttgatgac gagcgtaatg gctggcctgt tgaacaagtc tggaaagaaa    540
tgcataaact tttgccattc tcaccggatt cagtcgtcac tcatggtgat ttctcacttg    600
ataaccttat ttttgacgag gggaaattaa taggttgtat tgatgttgga cgagtcggaa    660
tcgcagaccg ataccaggat cttgccatcc tatggaactg cctcggtgag ttttctcctt    720
cattacagaa acggcttttt caaaaatatg gtattgataa tcctgatatg aataaattgc    780
agtttcattt gatgctcgat gagttttttct aagaattaat tcatgagcgg atacatattt    840
gaatgtattt agaaaaataa acaaataggg gttccgcgca catttccccg aaaagtgcca    900
cctgaaattg taaacgttaa tattttgtta aaattcgcgt taaatttttg ttaaatcagc    960
tcatttttta accaataggc cgaaatcggc aaaatccctt ataaatcaaa agaatagacc   1020
gagatagggt tgagtgttgt tccagtttgg aacaagagtc cactattaaa gaacgtggac   1080
tccaacgtca aagggcgaaa aaccgtctat cagggcgatg gcccactacg tgaaccatca   1140
ccctaatcaa gttttttggg gtcgaggtgc cgtaaagcac taaatcggaa ccctaaaggg   1200
agcccccgat ttagagcttg acggggaaag ccggcgaacg tggcgagaaa ggaagggaag   1260
aaagcgaaag gagcgggcgc tagggcgctg gcaagtgtag cggtcacgct gcgcgtaacc   1320
accacacccg ccgcgcttaa tgcgccgcta cagggcgcgt cccattcgcc aatccggagt   1380
cgactcctcc tttcgctagc aaaaaacccc tcaagacccg tttagaggcc caagggggtt   1440
atgctagtta ttgctcagcg gtggcagcag ccaactcagc ttcctttact agtttgttag   1500
cagccggatc tcagtggtgg tggtggtggt gctcgagtgc ggccgcaagc ttgtagacgg   1560
agctcgaatt cggatccgcg acccatttgc tgtccaccag tcatgcttgc catatggctg   1620
ccgcgcggca ccaggccgct gctgtgatga tgatgatgat ggctgctgcc catggtatat   1680
ctccttctta agttaaaca aaattatttc tagaggggaa ttgttatccg ctcacaattc   1740
ccctatagtg agtcgtatta atttcgcggg atcgagatct cgatcctcta cgccggacgc   1800
atcgtggccg gcatcaccgg cgcctaggtg cggttgctgg cgcctatatc gccgacatca   1860
ccgatgggga agatcgggct cgccacttcg ggctcatgag cgcttgtttc ggcgtgggta   1920
tggtggcagg ccccgtggcc ggggactgt tgggcgccat ctccttgcat gcaccattcc    1980
ttgcggcggc ggtgctcaac ggcctcaacc tactactggg ctgcttccta atgcaggagt   2040

```
cgcataaggg agagcgtcga gatcccggac accatcgaat ggcgcaaaac ctttcgcggt    2100
atggcatgat agcgcccgga agagagtcaa ttcagggtgg tgaatgtgaa accagtaacg    2160
ttatacgatg tcgcagagta tgccggtgtc tcttatcaga ccgtttcccg cgtggtgaac    2220
caggccagcc acgtttctgc gaaaacgcgg gaaaaagtgg aagcggcgat ggcggagctg    2280
aattacattc ccaaccgcgt ggcacaacaa ctggcgggca aacagtcgtt gctgattggc    2340
gttgccacct ccagtctggc cctgcacgcg ccgtcgcaaa ttgtcgcggc gattaaatct    2400
cgcgccgatc aactgggtgc cagcgtggtg gtgtcgatgg tagaacgaag cggcgtcgaa    2460
gcctgtaaag cggcggtgca caatcttctc gcgcaacgcg tcagtgggct gatcattaac    2520
tatccgctgg atgaccagga tgccattgct gtggaagctg cctgcactaa tgttccggcg    2580
ttatttcttg atgtctctga ccagacaccc atcaacagta ttattttctc ccatgaagac    2640
ggtacgcgac tgggcgtgga gcatctggtc gcattgggtc accagcaaat cgcgctgtta    2700
gcgggcccat taagttctgt ctcggcgcgt ctgcgtctgg ctggctggca taaatatctc    2760
actcgcaatc aaattcagcc gatagcggaa cgggaaggcg actggagtgc catgtccggt    2820
tttcaacaaa ccatgcaaat gctgaatgag ggcatcgttc ccactgcgat gctggttgcc    2880
aacgatcaga tggcgctggg cgcaatgcgc gccattaccg agtccgggct gcgcgttggt    2940
gcggatatct cggtagtggg atacgacgat accgaagaca gctcatgtta tatcccgccg    3000
ttaaccacca tcaaacagga ttttcgcctg ctggggcaaa ccagcgtgga ccgcttgctg    3060
caactctctc agggccaggc ggtgaagggc aatcagctgt tgcccgtctc actggtgaaa    3120
agaaaaacca ccctggcgcc caatacgcaa accgcctctc ccgcgcgtt ggccgattca     3180 ttaatgcagc tggcacgaca ggtttcccga ctggaaagcg ggcagtgagc gcaacgcaat    3240
taatgtaagt tagctcactc attaggcacc gggatctcga ccgatgccct tgagagcctt    3300
caacccagtc agctccttcc ggtgggcgcg gggcatgact atcgtcgccg cacttatgac    3360
tgtcttcttt atcatgcaac tcgtaggaca ggtgccggca gcgctctggg tcattttcgg    3420
cgaggaccgc tttcgctgga gcgcgacgat gatcggcctg tcgcttgcgg tattcggaat    3480
cttgcacgcc ctcgctcaag ccttcgtcac tggtcccgcc accaaacgtt tcggcgagaa    3540
gcaggccatt atcgccggca tggcggcccc acgggtgcgc atgatcgtgc tcctgtcgtt    3600
gaggacccgg ctaggctggc ggggttgcct tactggttag cagaatgaat caccgatacg    3660
cgagcgaacg tgaagcgact gctgctgcaa aacgtctgcg acctgagcaa caacatgaat    3720
ggtcttcggt ttccgtgttt cgtaaagtct ggaaacgcgg aagtcagcgc cctgcaccat    3780
tatgttccgg atctgcatcg caggatgctg ctggctaccc tgtggaacac ctacatctgt    3840
attaacgaag cgctggcatt gaccctgagt gattttctc tggtcccgcc gcatccatac     3900
cgccagttgt ttaccctcac aacgttccag taaccgggca tgttcatcat cagtaacccg    3960
tatcgtgagc atcctctctc gtttcatcgg tatcattacc cccatgaaca gaaatccccc    4020
ttacacggag gcatcagtga ccaaacagga aaaaccgcc cttaacatgg cccgctttat     4080
cagaagccag acattaacgc ttctggagaa actcaacgag ctggacgcgg atgaacaggc    4140
agacatctgt gaatcgcttc acgaccacgc tgatgagctt taccgcagct gcctcgcgcg    4200
tttcggtgat gacggtgaaa acctctgaca catgcagctc ccggagacgg tcacagcttg    4260
tctgtaagcg gatgccggga gcagacaagc ccgtcagggc gcgtcagcgg gtgttggcgg    4320
gtgtcggggc gcagccatga cccagtcacg tagcgatagc ggagtgtata ctggcttaac    4380
```

```
tatgcggcat cagagcagat tgtactgaga gtgcaccata tatgcggtgt gaaataccgc    4440
acagatgcgt aaggagaaaa taccgcatca ggcgctcttc cgcttcctcg ctcactgact    4500
cgctgcgctc ggtcgttcgg ctgcggcgag cggtatcagc tcactcaaag gcggtaatac    4560
ggttatccac agaatcaggg gataacgcag gaaagaacat gtgagcaaaa ggccagcaaa    4620
aggccaggaa ccgtaaaaag gccgcgttgc tggcgttttt ccataggctc cgcccccctg    4680
acgagcatca caaaaatcga cgctcaagtc agaggtggcg aaacccgaca ggactataaa    4740
gataccaggc gtttccccct ggaagctccc tcgtgcgctc tcctgttccg accctgccgc    4800
ttaccggata cctgtccgcc tttctccctt cgggaagcgt ggcgctttct catagctcac    4860
gctgtaggta tctcagttcg gtgtaggtcg ttcgctccaa gctgggctgt gtgcacgaac    4920 ccccgttca gcccgaccgc tgcgccttat ccggtaacta tcgtcttgag tccaacccgg    4980
taagacacga cttatcgcca ctggcagcag ccactggtaa caggattagc agagcgaggt    5040
atgtaggcgg tgctacagag ttcttgaagt ggtggcctaa ctacggctac actagaagga    5100
cagtatttgg tatctgcgct ctgctgaagc cagttacctt cggaaaaaga gttggtagct    5160
cttgatccgg caaacaaacc accgctggta gcggtggttt ttttgtttgc aagcagcaga    5220
ttacgcgcag aaaaaaagga tctcaagaag atcctttgat cttttctacg ggtctgacg    5280 ctcagtggaa cgaaaactca cgttaaggga ttttggtcat gaacaataaa actgtctgct    5340
tacataaaca gtaatacaag gggtgttatg a                                  5371

<210> SEQ ID NO 6
<211> LENGTH: 43
<212> TYPE: DNA
<213> ORGANISM: Artificial Sequence
<220> FEATURE:
<223> OTHER INFORMATION: DNA Primer

<400> SEQUENCE: 6
ttcgagctcg gtacccgggg atccatgagc aaaacccagg aat                     43

<210> SEQ ID NO 7
<211> LENGTH: 38
<212> TYPE: DNA
<213> ORGANISM: Artificial Sequence
<220> FEATURE:
<223> OTHER INFORMATION: DNA Primer

<400> SEQUENCE: 7
agacatagaa ccaccaccca gtttccaggt gacgtggc                           38

<210> SEQ ID NO 8
<211> LENGTH: 32
<212> TYPE: DNA
<213> ORGANISM: Artificial Sequence
<220> FEATURE:
<223> OTHER INFORMATION: DNA Primer

<400> SEQUENCE: 8
ggtggtggtt ctatgtctca ggttcagagt gg                                 32

<210> SEQ ID NO 9
<211> LENGTH: 43
<212> TYPE: DNA
<213> ORGANISM: Artificial Sequence
<220> FEATURE:
<223> OTHER INFORMATION: DNA Primer

<400> SEQUENCE: 9
```
aaaacgacgg ccagtgccaa gcttttacag cgccatcaac ttg         43

<210> SEQ ID NO 10
<211> LENGTH: 25
<212> TYPE: DNA
<213> ORGANISM: Artificial Sequence
<220> FEATURE:
<223> OTHER INFORMATION: DNA Primer

<400> SEQUENCE: 10
ccgggtaccg agctcgaatt cgtaa         25

<210> SEQ ID NO 11
<211> LENGTH: 25
<212> TYPE: DNA
<213> ORGANISM: Artificial Sequence
<220> FEATURE:
<223> OTHER INFORMATION: DNA Primer

<400> SEQUENCE: 11
ggcactggcc gtcgttttac aacgt         25

<210> SEQ ID NO 12
<211> LENGTH: 43
<212> TYPE: DNA
<213> ORGANISM: Artificial Sequence
<220> FEATURE:
<223> OTHER INFORMATION: DNA Primer

<400> SEQUENCE: 12
ttcgagctcg gtacccgggg atccatgtct caggttcaga gtg         43

<210> SEQ ID NO 13
<211> LENGTH: 38
<212> TYPE: DNA
<213> ORGANISM: Artificial Sequence
<220> FEATURE:
<223> OTHER INFORMATION: DNA Primer

<400> SEQUENCE: 13
gctcatagaa ccaccaccca gcgccatcaa cttgtcca         38

<210> SEQ ID NO 14
<211> LENGTH: 37
<212> TYPE: DNA
<213> ORGANISM: Artificial Sequence
<220> FEATURE:
<223> OTHER INFORMATION: DNA Primer

<400> SEQUENCE: 14
ggtggtggtt ctatgagcaa aacccaggaa tttcgtc         37

<210> SEQ ID NO 15
<211> LENGTH: 43
<212> TYPE: DNA
<213> ORGANISM: Artificial Sequence
<220> FEATURE:
<223> OTHER INFORMATION: DNA Primer

<400> SEQUENCE: 15
aaaacgacgg ccagtgccaa gcttttacag tttccaggtg acg         43

<210> SEQ ID NO 16
<211> LENGTH: 34
<212> TYPE: DNA

```
<213> ORGANISM: Artificial Sequence
<220> FEATURE:
<223> OTHER INFORMATION: DNA Primer

<400> SEQUENCE: 16
cgcggatcca tgtctcaggt tcagagtggc attt                               34

<210> SEQ ID NO 17
<211> LENGTH: 37
<212> TYPE: DNA
<213> ORGANISM: Artificial Sequence
<220> FEATURE:
<223> OTHER INFORMATION: DNA Primer

<400> SEQUENCE: 17
cccaagcttt tacagcgcca tcaacttgtc cagcgac                            37
```